(12) United States Patent
Das (10) Patent No.: US 8,972,460 B2
(45) Date of Patent: Mar. 3, 2015

(54) DATA MODEL OPTIMIZATION USING MULTI-LEVEL ENTITY DEPENDENCIES

(71) Applicant: Oracle International Corporation, Redwood Shores, CA (US)

(72) Inventor: Pradipta Das, Hyderabad (IN)

(73) Assignee: Oracle International Corporation, Redwood Shores, CA (US)

( * ) Notice: Subject to any disclaimer, the term of this patent is extended or adjusted under 35 U.S.C. 154(b) by 130 days.

(21) Appl. No.: 13/658,651

(22) Filed: Oct. 23, 2012

(65) Prior Publication Data

US 2014/0115012 A1   Apr. 24, 2014

(51) Int. Cl.
*G06F 17/30* (2006.01)

(52) U.S. Cl.
USPC ............................................... 707/803

(58) Field of Classification Search
CPC ............... G06F 17/30292; G06F 17/30294; G06F 17/30604
USPC ................................. 707/796, 802, 803, 810
See application file for complete search history.

(56) References Cited

U.S. PATENT DOCUMENTS

| | | | |
|---|---|---|---|
| 7,664,729 B2* | 2/2010 | Klein et al. ................ | 707/791 |
| 7,831,632 B2* | 11/2010 | Djugash et al. ............ | 707/803 |
| 8,010,570 B2* | 8/2011 | Sweeney ..................... | 707/791 |
| 8,195,698 B2* | 6/2012 | Wasserman et al. ........ | 707/793 |
| 8,443,074 B2* | 5/2013 | Bahl et al. .................. | 709/224 |
| 8,661,111 B1* | 2/2014 | Lauckhart et al. .......... | 709/224 |
| 2003/0084425 A1* | 5/2003 | Glaser ......................... | 717/110 |
| 2005/0027542 A1* | 2/2005 | Bordawekar et al. ....... | 705/1 |
| 2005/0027845 A1* | 2/2005 | Secor et al. ................. | 709/223 |
| 2005/0149484 A1* | 7/2005 | Fox et al. .................... | 707/1 |
| 2006/0235835 A1* | 10/2006 | Dettinger et al. ............ | 707/4 |
| 2008/0162207 A1* | 7/2008 | Gross et al. ................. | 705/7 |
| 2010/0030774 A1* | 2/2010 | Dettinger et al. ........... | 707/5 |
| 2012/0136868 A1* | 5/2012 | Hammerschmidt et al. .. | 707/741 |
| 2012/0271604 A1* | 10/2012 | Jain et al. ................... | 703/6 |

* cited by examiner

*Primary Examiner* — Cam-Linh Nguyen (74) *Attorney, Agent, or Firm* — Vista IP Law Group, LLP (57) ABSTRACT

A method, system, and computer program product for of database schema management. The computer implemented method for data model optimization using multilevel entity dependency analytics commences by accessing a multilevel schema data structure, determining the relationship lineages present in the multilevel schema data structure and generating a dependency table using the relationship lineage. Then, using the dependency table the computer implemented method performs at least one of, a high impact analysis, a referential integrity analysis, or a conformance analysis. In some embodiments the results of the analysis are reported to a user and in some embodiments the results of the analysis applied to the multilevel schema data structure.

20 Claims, 7 Drawing Sheets

DATA MODEL OPTIMIZATION USING MULTI-LEVEL ENTITY DEPENDENCIES

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD

The disclosure relates to the field of database schema and data model management and more particularly to techniques for optimizing underlying data models.

BACKGROUND

Some embodiments of the present disclosure are directed to an improved approach for implementing data model optimization using multilevel entity dependency analytics.

In the process of developing database schema, and in the process of maintaining databases based on such schema, database engineers (e.g., data modelers) often need detailed insight into dependencies between parent child entities within a schema. Although some legacy tools have attempted to address this need, a vast chasm exists between the legacy offerings and the multilevel analytics needed to make optimization decisions pertaining to multilevel dependencies between parent child entities within a schema.

Moreover, the aforementioned technologies do not have the capabilities to perform data model optimization using multilevel entity dependency analytics. Therefore, there is a need for an improved approach.

SUMMARY

The present disclosure provides an improved method, system, and computer program product suited to address the aforementioned issues with legacy approaches. More specifically, the present disclosure provides a detailed description of techniques used in methods, systems, and computer program products for data model optimization using multilevel entity dependency analytics.

The method for data model optimization using multilevel entity dependency analytics commences by accessing a multilevel schema data structure, determining the relationship lineages present in the multilevel schema data structure and generating a dependency table using the relationship lineage. Then, using the dependency table the computer implemented method performs at least one of, a high impact analysis, a referential integrity analysis, or a conformance analysis. In some embodiments the results of the analysis are reported to a user and in some embodiments the results of the analysis applied to the multilevel schema data structure.

Further details of aspects, objectives, and advantages of the disclosure are described below in the detailed description, drawings, and claims. Both the foregoing general description of the background and the following detailed description are exemplary and explanatory, and are not intended to be limiting as to the scope of the claims.

DETAILED DESCRIPTION

Some embodiments of the present disclosure are directed to an improved approach for implementing data model optimization using multilevel entity dependency analytics. More particularly, disclosed herein are exemplary environments, methods, and systems.

Overview

Described herein-below and in the accompanying figures are scalable methods and apparatus for implementing data model optimization using multilevel entity dependency analytics.

The figures and corresponding discussions disclose techniques for performing and reporting multilevel analytics needed to make optimization decisions pertaining to multilevel dependencies between parent child entities within a schema. Several of the herein-disclosed systems are capable of supporting data model optimization for both "online transactional process (OLTP)" as well as for "online analytical process (OLAP)", and/or wherever aspects of referential integrity emerge as important characteristics of the schema. One exemplary embodiment pertains to the "data warehousing" domain, which domain is sometimes categorized within "online analytical process (OLAP)".

In the enterprise data warehousing domain, operating a data warehouse often comprises activities involving requirements for gathering data, schema development, data importing, query optimization, and roll-out to a production environment. In most of the aforementioned activities there has emerged a need to perform analytics on an actual or prophetic schema. Some such analytics include herein disclosed quantitative methods for:

- Identification of "High Impact Entities (HIE)" to analyze the impact of data model changes.
- Identification of "Circular Referential Integrity (CRI)" and "Redundant Referential Integrity (RRI)" to facilitate removal of relationship anomalies found in a data model.
- Identification of "Conformed Entities (CE)" for development of conformed "data marts".
- 4. Identification of "Entity Loading Sequence (ELS)" before loading data into target schema for prompt data dependency check and improve overall data loading time (e.g., by loading entities in ascending order of their loading sequence will resolve data dependency must faster, no other validation on referential integrity will be needed.) Identification of tables that can become candidates for parallel loading order exploitation. Such exploitation can be used for spawning parallel threads in expectation to ensure better resource utilization.

Further, techniques for reporting the findings of the analytics are needed, and thus also disclosed are techniques for generation of reports in various forms, including a "Multilevel Entity Dependency Matrix (MEDM)".

The above address myriad deficiencies with legacy techniques. Strictly as examples, legacy techniques were only able to report on a single level of a parent-child dependency. Legacy techniques failed to address the requirement of identifying "High Impact Entities (HIE)", "Conformed Entities (CE)", "Circular Referential Integrity (CRI)", and "Redundant Referential Integrity (RRI)". In some cases legacy tools partially addressed some of the aforementioned requirements, however all such legacy tools exhibited deficiencies in usability in that such legacy tools were not scalable. The techniques disclosed herein overcome such scalability deficiencies in that system embodiments of the present disclosure can process huge data models (e.g., "third normal form" 3NF Data Models such as "Healthcare Data Warehouse Foundation" HDWF) where the number of tables approaches the thousands (or larger) and where there are thousands (or many thousands) of relationships.

User Insight

The approach herein results in analysis results and reports (e.g., a "Multilevel Entity Dependency Matrix (MEDM)" that facilitates the development of user insight. For example, some such analysis results and reporting offers visibility into multilevel foreign key references that are used to populate target tables. Strictly as an example, during the definition of a particular table, a data modeler might want to know which other tables must also be populated, and with what data items. The term dependency within the meaning of the disclosure herein can include a variety of different meanings (which may become a column heading in an output matrix). Some examples (which are discussed in further detail below) for dependency matrix column headings include:

rootChildTable,
childTable,
immediateParentTable,
depth, and
optionality.

System embodiments as herein disclosed provided fully automated features that are customizable by a user. For example, a particular user can choose to work on a specific set of business processes within a schema, while unencumbered by aspects of schema that are outside of the scope and focus of that particular user's focus. Such automated features facilitate determination of impact of subsequent change requests.

Additionally, the embodiments of the accompanying figures and discussions (e.g., see the dependency analytics engine of FIG. 1) implement significant technical advances as follows:

The analytics engine identifies useful parameters and quantifies them for better assessment of key features of data model design.
The analytics engine and its output reports helps data modelers to optimize data model design with respect to referential integrities.
Certain modules of the analytics engine analyze data dependency among parent child entities, and such dependencies are analyzed across multiple levels of hierarchy.

Scripting and query language-based procedures support automated processing and reprocessing (e.g., including regression testing).

DEFINITIONS

Some of the terms used in this description are defined below for easy reference. The presented terms and their respective definitions are not rigidly restricted to these definitions—a term may be further defined by the term's use in within this disclosure.

A data warehouse is subject oriented, integrated, time-variant and non-volatile collection of data in support of business analytics and decision support system. It refers to the practice of storing a large amount of information in logical proximity so as to facilitate complex queries, even across domains. A data warehouse can be of third normal form 3NF (e.g., enterprise data warehouse used for organization level information management) which includes all aspects of relational data base schema.

The term "metadata" refers to data about other data.

The acronym "HDWF" refers to Healthcare Data Warehouse Foundation, an integrated analytical solution that integrates multiple dependent sources into a single enterprise data warehouse, enabling data analytics, master data management and business decision support system.

The term "design patterns" refers to standard design methodologies or best practices used to define the data architecture of entity, attributes and dependencies among multiple entities during data modeling activities. Patterns are defined based on certain process commonalities such as, "One-To-One", "One-To-Many", "Super-Type/Sub-Type", "Intersection" etc. Entities within a schema can be classified under such design patterns.

The term "logic" means any combination of software or hardware that is used to implement all or part of the embodiments of the present disclosure.

A "module" includes any mix of any portions of computer memory and any extent of circuitry including hardwired logic or circuitry embodied as a processor.

Reference is now made in detail to certain embodiments. The disclosed embodiments are not intended to be limiting of the claims.

DESCRIPTIONS OF EXEMPLARY EMBODIMENTS

Figure 1:
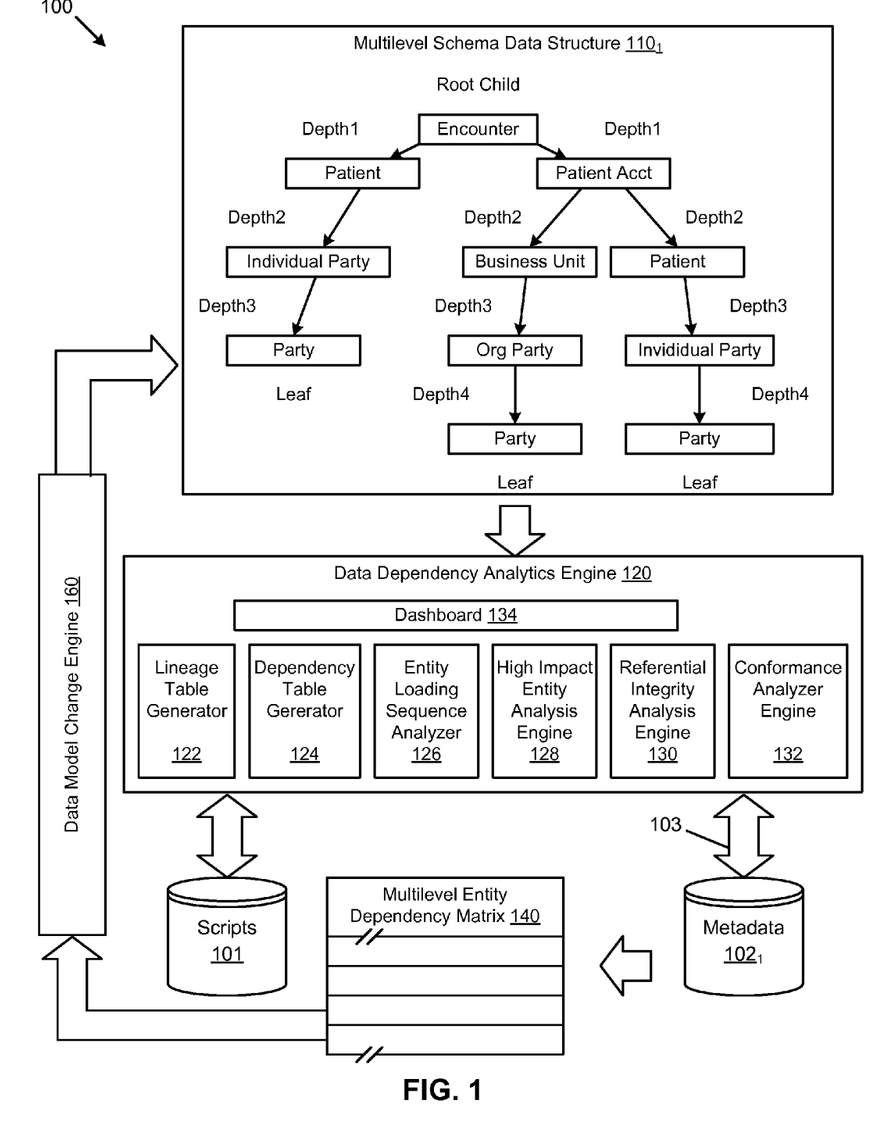
FIG. 1 is a system for performing data model optimization using multilevel entity dependency analytics, according to some embodiments.

FIG. 1 is a system 100 for performing data model optimization using multilevel entity dependency analytics. As an option, the present system 100 may be implemented in the context of the architecture and functionality of the embodiments described herein. Also, the system 100 or any aspect therein may be implemented in any desired environment.

As shown, the aforementioned approaches use a computer-implemented method (e.g., see data dependency analytics engine 120), to perform analyses and produces outputs in the form of metadata and reports (e.g., a multilevel entity dependency matrix 140). The outputs (e.g., outputs that facilitate the development of user insight can come in the form of the aforementioned reports, or can come in the form of metadata (e.g., metadata $102_1$) that is used by other components. Any metadata can arise from outputs of the data dependency analytics engine 120 and/or any constituent components. Moreover any metadata can be read by the data dependency analytics engine 120 and/or any constituent components. As shown, an instance of a multilevel entity dependency matrix

140 (or interim version of same) can be derived from metadata, and can be read by the data dependency analytics engine 120 and/or any constituent components.

The writing and reading of metadata is a convenient way for constituent components to communicate one with another, although such a technique is not the only technique possible. In exemplary embodiments the metadata is stored and/or communicated in one or more of the following metadata formats:

- an XML format,
- a binary format,
- a message format,
- a relational database table.

Multilevel Entity Dependency Matrix (MEDM)

Now, turning attention to characteristics of the shown multilevel entity dependency matrix (also referred to as "dependency matrix", or just "matrix"), the matrix can support any number of columns and/or rows. Strictly as examples, metadata of an exemplary dependency matrix column headings might include:

- rootChildTable,
- childTable,
- immediateParentTable,
- depth, and
- optionality.

The dependency matrix serves to provide detailed analysis of multilevel dependencies by populating each and every HDWF table (that is, before a table can be populated, which other tables must be populated). In the dependency matrix, for each table, a cell in a row of the matrix (e.g., in a column labeled 'SEQ') is assigned values describing the dependency level of a subject table. The value or values are based on the total levels of 'parent' tables that need to be populated before the subject table can be populated:

For example, and referring to the schema given in the multilevel schema data structure 110₁, before populating the "Patient" table, the "Individual Party" table must be populated, thus the "Individual Party" table is deemed to be a first level parent for the Patient table. Similarly for populating Individual Party, Party must be populated (second level parent with respect to Patient) and Party can be populated without populating any other table (e.g., since it is a leaf of the schema). Based on this information, the following sequence numbers are assigned:

Party=0, Individual Party=1, Patient=2

Since there can be multiple parental paths for any table, the longest path is used to assign the dependency level to the table. For example the "Encounter" table has multiple parental paths, two of which are mentioned below.

Path 1: Encounter (3)<=Patient (2)<=Individual Party (1)<=Party (0)

Path 2: Encounter (4)<=Patient Account (3)<=Business Unit (2)<=Organization Party (1)<=Party (0)

Based on the above dependency information, dependency level 4 is assigned to Encounter.

Exemplary Derivation Steps

Step 1: Generate a report (see Table 1) enumerating each child and its immediate parent table with a corresponding optionality attribute. This attribute captures the lineage between two entities based on foreign key references. The report can be generated directly from a schema querying user constraints system views. In some cases the corresponding optionality attribute is derived from user constraints as well.

TABLE 1

Example enumerating optionality of each child and its immediate parent

| Child_Table | Parent_Table | Optionality |
|---|---|---|
| HDM_ENC | HDM_PT | N |
| HDM_ENC | HDM_PT_ACCT | Y |
| HDM_PT | HDM_IND_PRTY | N |
| HDM_PT_ACCT | HDM_PT | N |
| HDM_IND_PRTY | HDM_PRTY | N |
| HDM_PRTY | NULL | NULL |
| HDM_PT_ACCT | HDM_BIZ_UNT | Y |
| HDM_BIZ_UNT | HDM_ORG_PRTY | N |
| HDM_ORG_PRTY | HDM_PRTY | N |
| ... | ... | ... |

Step 2: Generate a dependency matrix row for each table within a schema that represents multiple parental paths and depth. As shown in Table 2, the column "Root_Child_Table" was generated using a CONNECT BY clause being operated on the report that was generated in Step 1. An example (in pseudo code) is given below:

Pseudo Code—Derivation of Dependency Tree:

```
...
BEGIN
    FOR X IN (LIST TABLE_NAME ACROSS
    SCHEMA ='$SCHEMA_NAME')
    LOOP
    FOR T IN (LIST DISTINCT PARENT_TABLE, CHILD_TABLE,
LEVEL AS DEPTH, NULLABLE
        FROM TABLE1 START WITH CHLD_TBL =
        X.TABLE_NAME
            CONNECT BY NOCYCLE CHLD_TBL = PRIOR
PAR_TBL ORDER BY DEPTH, CHLD_TBL
        )
    LOOP
        INSERT INTO TABLE2 (ROOT_CHILD_TBL, CHILD_TBL,
IMMIDIATE_PARENT, DEPTH, OPTIONAL )
        VALUES(X.TABLE_NAME, T.CHLD_TBL, T.PAR_TBL,
T.DEPTH, T.NULLABLE);
        END LOOP;
END LOOP;
COMMIT;
END;
```

This will give Child and immediate Parent (with proper depth) of the Parent with respect to the Root_Child_Table for each branch of relationship in the schema.

TABLE 2

Example showing branches of relationships in the schema

| Root_Child_Table | Child_Table | Immediate_Parent | Depth | Optionality |
|---|---|---|---|---|
| HDM_ENC | HDM_ENC | HDM_PT | 1 | N |
| HDM_ENC | HDM_ENC | HDM_PT_ACCT | 1 | Y |
| HDM_ENC | HDM_PT | HDM_IND_PRTY | 2 | N |
| HDM_ENC | HDM_PT_ACCT | HDM_PT | 2 | N |
| HDM_ENC | HDM_IND_PRTY | HDM_PRTY | 3 | N |
| HDM_ENC | HDM_PRTY | NULL | 4 | NULL |

TABLE 2-continued

Example showing branches of relationships in the schema

| Root_Child_Table | Child_Table | Immediate_Parent | Depth | Optionality |
|---|---|---|---|---|
| HDM_ENC | HDM_PT | HDM_IND_PRTY | 3 | N |
| HDM_ENC | HDM_IND_PRTY | HDM_PRTY | 4 | N |
| HDM_ENC | HDM_PRTY | NULL | 5 | NULL |
| HDM_ENC | HDM_PT_ACCT | HDM_BIZ_UNT | 2 | Y |
| HDM_ENC | HDM_BIZ_UNT | HDM_ORG_PRTY | 3 | N |
| HDM_ENC | HDM_ORG_PRTY | HDM_PRTY | 4 | N |
| HDM_ENC | HDM_PRTY | NULL | 5 | NULL |
| ... | ... | ... | ... | ... |

In the above dependency matrix for Encounter (e.g., shown as HDM_ENC) given as a root child table, it has two immediate parents, namely "Patient" and "Patient Account" both at level 1 (see row 1 and row 2 of Table 2). This shows two different branches of relationships starting from Encounter, down to a leaf table, in this case "Party". "Patient Account" also has two different branches of relationships, namely "Patient" and "Business Unit" as shown in the Table 2 and FIG. 1.

Once populated, a dependency tree will exists for each HDWF table.

Also, for each table, a dependency level known as "Entity Loading Sequence (ELS)" is generated based on the total number parent levels that need to be populated before a subject table can be populated. Further techniques for using "Entity Loading Sequence" are discussed infra.

The aforementioned techniques for generating a dependency matrix having a "Root_Child_Table" column and an "Entity Loading Sequence" can be implemented by a computer. For example, constituent analysis modules within a data dependency analytics engine can generate a dependency matrix. In some cases, outputs of the data dependency analytics engine 120 are used by a data model change engine 160, which data model change engine can serve to highlight recommended changes in a dashboard 134, which dashboard in turn, a user can use to make changes or evaluate alternatives. As earlier indicated, scripting and query language-based procedures support automated processing and reprocessing (e.g., including regression testing); such scripts 101 can be read and/or written by the data dependency analytics engine 120 (e.g., see path 103), and can be used to facilitate automated processing including regression testing.

Figure 2:
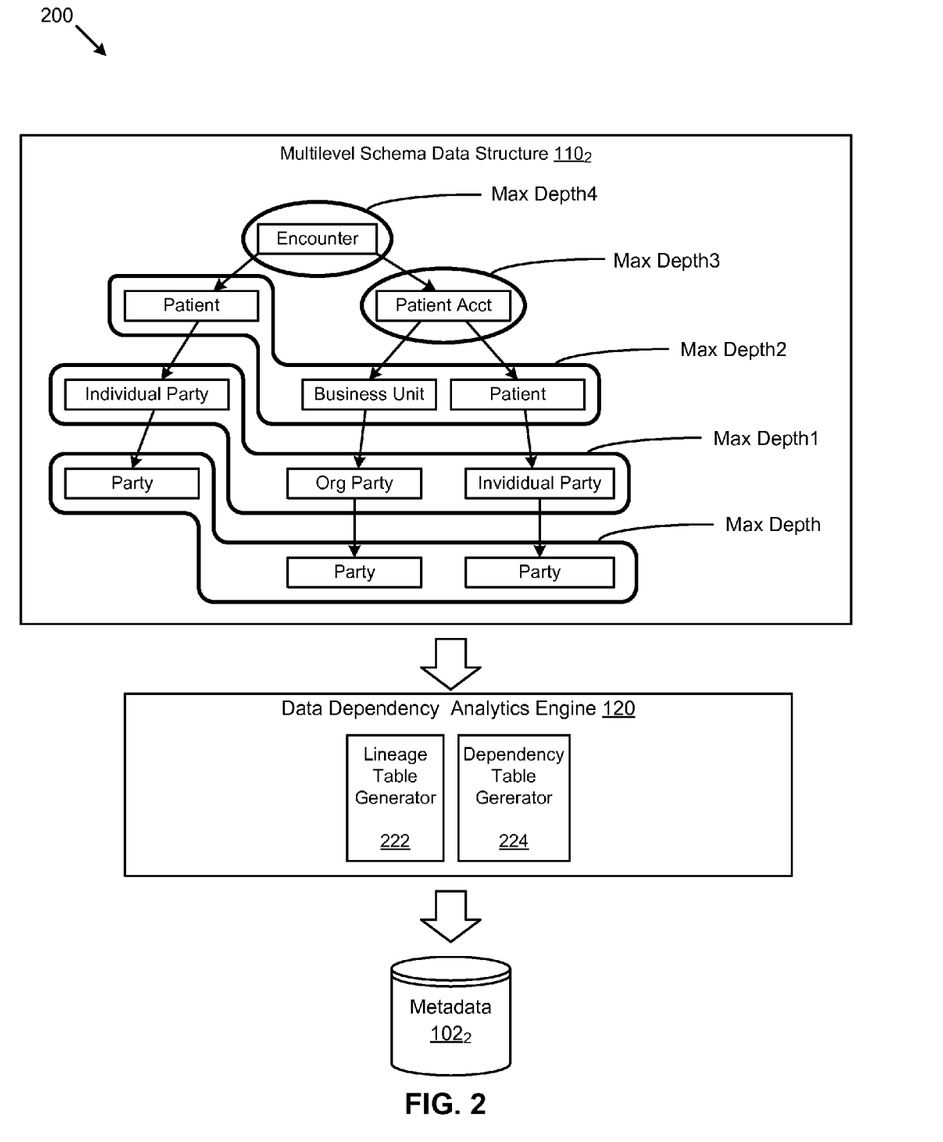
FIG. 2 is a simplified representation of a schema to serve as an example for performing data model optimization using multilevel entity dependency analytics, according to some embodiments.

As shown, the lineage table generator 222 and the dependency table generator 224 can calculate and supply outputs that are taken as inputs into an entity loading sequence analyzer 126, a high impact entity analysis engine 128, a referential integrity analysis engine 130, and/or a conformance analyzer engine 132, each of which are discussed as pertaining to the following figures.

FIG. 2 is a simplified representation of a schema 200 to serve as an example for performing data model optimization using multilevel entity dependency analytics. As an option, the present schema 200 may be implemented in the context of the architecture and functionality of the embodiments described herein. Also, the schema 200 or any aspect therein may be implemented in any desired environment.

As shown, the multilevel schema data structure $110_2$ is an annotated version of multilevel schema data structure $110_1$. The annotations serve to elucidate the performance of steps to calculate overall loading sequence i.e., "Entity Loading Sequence (ELS)" for each table by using the depth of occurrences of each table across all the branches of relationships derived by the dependency table generator 124. Each table is assigned a loading sequence number depending upon their depth of occurrence across all the parental paths exist within the schema. In this embodiment, tables that occur at the maximum depth with respect to root child table in dependency tree of each parental branch will be assigned loading sequence number "0". Tables that occur at maximum depth −1 and had not been assigned any sequence number previously will be assigned loading sequence number "1". Similarly, tables that occur as a root at depth 0 and not being assigned any sequence before will have a maximum loading sequence. In more formal notation:

Table T will have SEQ NO=n
if and when:
   T occurs at Depth of {max (depth)−n} across all branches, and T is not already assigned any SEQ NO<n For example, referring to the multilevel schema data structure $110_2$, there are three different branches of relationship starting from "Encounter".

Encounter (0)>Patient (1)>Individual Party (2)>Party (3)
Encounter (0)>Patient Account (1)>Patient (2)>Individual Party (3)>Party (4)
Encounter (0)>Patient Account (1)>Business Unit (2)>Individual Party (3)>Party (4)

The above results are tabulated in the following Table 3.

TABLE 3

| Max(depth)-0 | Max(depth)-1 | Max(depth)-2 | Max(depth)-4 | Max(depth)-5 |
|---|---|---|---|---|
| SEQ NO = 0 | SEQ NO = 1 | SEQ NO = 2 | SEQ NO = 3 | SEQ NO = 4 |
| HDM_PRTY | HDM_IND_PRTY | HDM_PT | HDM_ENC | |
| HDM_PRTY | HDM_IND_PRTY | HDM_PT | HDM_PT_ACCT | HDM_ENC |
| HDM_PRTY | HDM_ORG_PRTY | HDM_BIZ_UNT | HDM_PT_ACCT | HDM_ENC |

Distinct Tables in SEQ NO=0 are HDM_PRTY
Distinct Tables in SEQ NO=1 are HDM_IND_PRTY, HDM_ORG_PRTY
Distinct Tables in SEQ NO=2 are HDM_PT, HDM_BIZ_UNT
Distinct Tables in SEQ NO=3 are HDM_PT_ACCT, HDM_ENC
Distinct Tables in SEQ NO=4 are HDM_ENC Pseudo code—Calculation of Entity Loading Sequence:

```
BEGIN
...
FOR I IN 0 TO MAX (DEPTH)_db [ACROSS ALL PARENTAL PATH
OF SCHEMA]
LOOP
FOR X IN (LIST ROOT_CHILD_TABLE, {MAX" (DEPTH)_root_child -
I} [GROUP BY ROOT_CHILD_TABLE] AS MAXDEPTH USING
TABLE1)
LOOP
...
LIST DISTINCT
CHILD_TABLE_NAME          AS TABLE_NAME,
X.I AS LOADING            AS SEQ_NO
USING TABLE2 WHERE TABLE2.ROOT_CHILD_TBL =
X.ROOT_CHILD_TBL AND TABLE1.DEPTH = X.MAXDEPTH AND
CHILD_TABLE_NAME NOT ASSIGNED SEQ_NO<X.I
...
END LOOP;
END LOOP;
END;
```

As can be seen through this example, "Encounter" appears in SEQ NO=3 and in SEQ NO=4, the loading logic can thus be applied to get minimum loading order which will satisfy dependency at any subsequent level. Optionality can also be taken into consideration. For example, in the case of considering "Encounter" to "Patient Account" as an optional relationship, then the SEQ NO will be 4. Else the SEQ will remain 3. In such a case the user can decide whether the optional relationship will be in use or not, and based on the user's determination, the overall loading sequence can be established.

Figure 3:
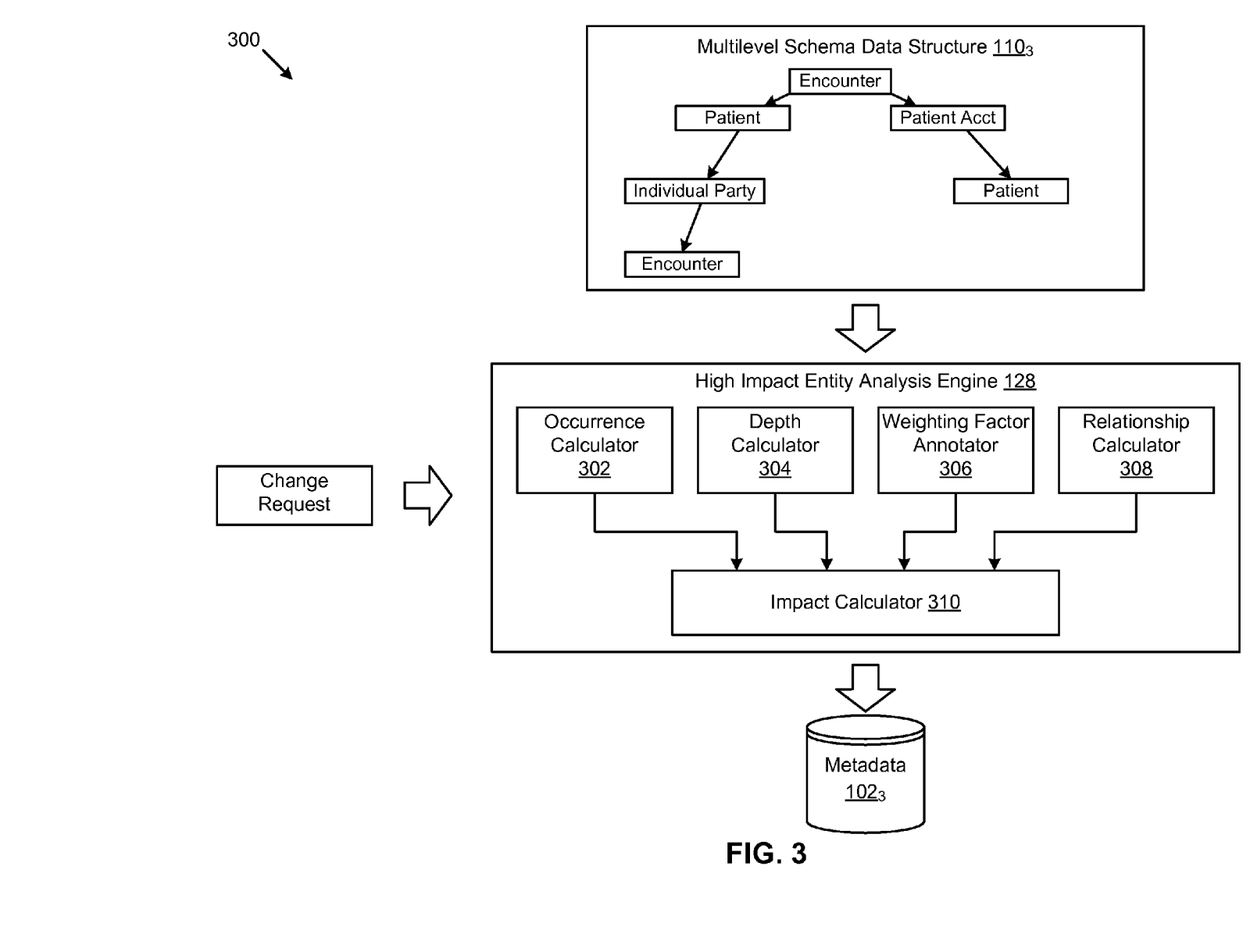
FIG. 3 depicts a high impact entity analyzer subsystem used in a system for data model optimization using multilevel entity dependency analytics, according to some embodiments.

FIG. 3 depicts a high impact entity analyzer subsystem 300 used in a system for data model optimization using multilevel entity dependency analytics. As an option, the present high impact entity analyzer subsystem 300 may be implemented in the context of the architecture and functionality of the embodiments described herein. Also, the high impact entity analyzer subsystem 300 or any aspect therein may be implemented in any desired environment.

As earlier indicated, some of the automated features as disclosed herein serve to facilitate determination of impact of change requests. One such automated feature is the determination of "High Impact Entities".

Specifically, metadata determined from and/or stored in a dependency matrix can be used to identify "High Impact Entities (HIE)", which is briefly discussed below.

High Impact Entity Analysis

In a complex relational data model, data modelers often face a situation where the data modeler needs to analyze the impact of removal of an entity, for example to prepare to deprecate (and later remove) the entity in subsequent releases. What is needed is to quantify the degree of impact for each such candidate entity before actually making changes. This situation becomes acute when the referential integrity of a concerned data model would be violated by the removal of a candidate high impact entity.

In the embodiments herein, one step to quantify the degree of impact of removal of an entity is to consider the number of occurrences of the candidate entity across multilevel relationships; that is, to consider how many relationship branches would be affected after the removal of the candidate high impact entity. A weightage factor can be added along with a count. In an exemplary case, the count value is a count of relationships based on the type design patterns used to create the entity. Also, the depth (e.g., number of children affected by the removal of a parent entity at any depth with respect to a child) is a factor to be considered to quantify the degree of impact of deprecation and/or removal of an entity. In some cases, the median depth of the subject entity with respect to a child by total number of occurrences across the relationships is calculated.

As shown, a high impact entity analysis engine 128 has constituent modules in the form of an occurrence calculator 302, a depth calculator 304, a weighting factor annotator 306, and a relationship calculator 308. Some or all of the aforementioned modules can output numeric values, and outputs from some or all of the aforementioned can be used by an impact calculator 310. Outputs from the impact calculator 310 can be stored in metadata $102_3$.

Illustration

Consider a schema containing the following four multilevel relationships (R1, R2, R3, and R4). What is needed is to quantify the degree of impact for removal of the entity B from the schema. As described above, design patterns associated with each and every entity that is going to define a weightage factor has been determined; see "Weightage(Wp)" in Table 4.

TABLE 4

| Entity(E) | Pattern(P) | Weightage(Wp) |
|---|---|---|
| A | One To One | 0.50 |
| B | Super Type | 0.99 |
| C | Sub Type | 0.25 |
| D | Intersection | 0.10 |
| E | One To One | 0.50 |
| F | One To One | 0.50 |
| G | One To One | 0.50 |
| H | One To One | 0.50 |
| I | One To One | 0.50 |
| M | One To One | 0.50 |
| ... | ... | ... |

Now, given the information of Table 4 as an input, the constituent of the high impact entity analysis engine 128 can calculate aspects of the multilevel relationships in the schema. Specifically:

The occurrence calculator 302 can calculate the number of occurrence of Entity B across all the relationships:
Nb=3 [R1, R2, R3]
Average depth of B with respect to child:
Db=3.33
A weightage factor assigned to B:
Wb=0.99
Relationships are calculated (e.g., using relationship calculator 308):
R1: A>B>C>0>E>F>G>H>I
   depth of B is 7 with respect to child
R2: A>X>Y>B>Z
   depth of B is 1 with respect to child
R3: M>N>B>0>P
   depth of B is 2 with respect to child
R4: A>Q>R>S>T>D Then, the degree of impact ascribed to the act of removing B is given by:

$$Ib = [\text{Number of Occurrences of } B(Nb) + \text{Weightage Factor}(Wb) + \text{Average Depth}(Db)] / [\text{Total Number}$$

of Relationships($N$max)+Maximum Weightage Factor($W$max)+Maximum Depth($D$max)].

In this example:

$$Ib=[3+0.99+3.33]/[4+1+8]=7.32/13=0.57$$

Thus each entity within a schema can be assigned a calculated degree of degree of impact value. In certain organizational settings, entities with a degree of impact over some value or greater will be deemed to be a "High Impact Entity" and removal of that entity would be discouraged or prohibited.

Figure 4:
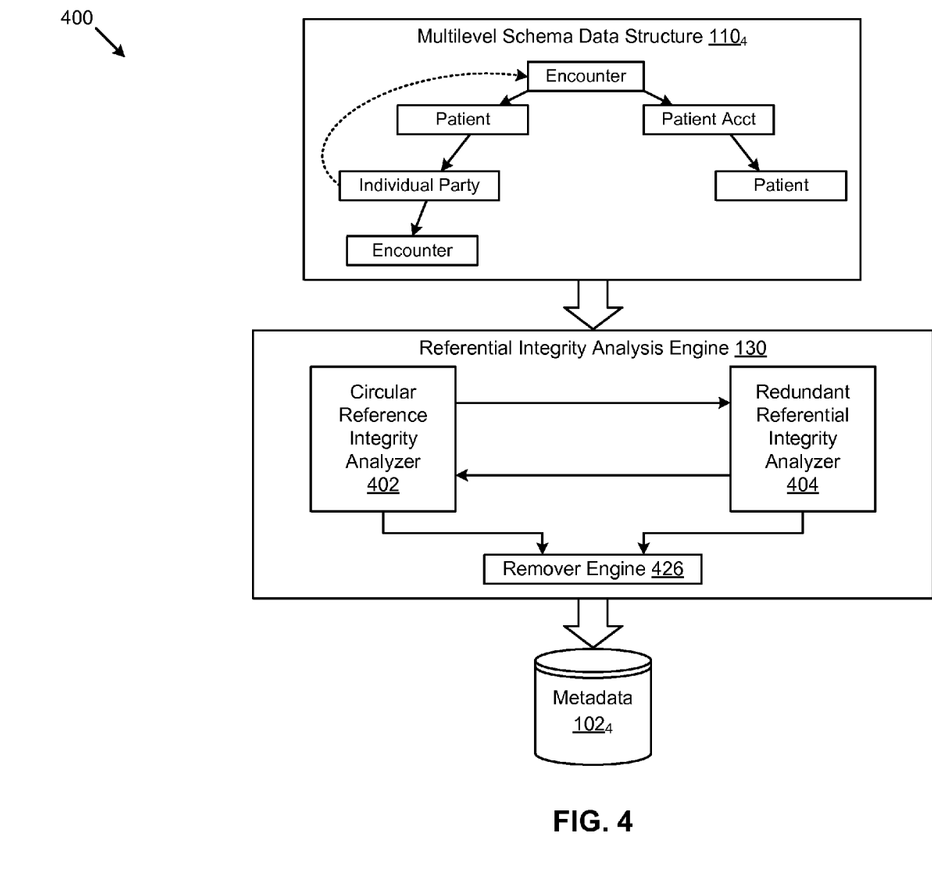
FIG. 4 depicts a referential integrity analyzer subsystem used in a system for data model optimization using multilevel entity dependency analytics, according to some embodiments.

FIG. 4 depicts a referential integrity analyzer subsystem 400 used in a system for data model optimization using multilevel entity dependency analytics. As an option, the present referential integrity analyzer subsystem 400 may be implemented in the context of the architecture and functionality of the embodiments described herein. Also, the referential integrity analyzer subsystem 400 or any aspect therein may be implemented in any desired environment.

As shown, a referential integrity analysis engine 130 includes a circular reference integrity analyzer 402 and a redundant referential integrity analyzer 404. The referential integrity analysis engine 130 can take in an input multilevel schema data structure $110_4$, and can output results in the form of metadata $102_4$.

Identification of Relational Anomalies in Physical Data Model

Information available from an instance of a multilevel entity dependency matrix can be used to detect anomalies related to entity relationships within a data model. Two of such anomalies are:

Circular Referential Integrity (CRI), and
Redundant Referential Integrity (RRI).

Circular references can cause a deadlock scenario where a table loading routine is not able to take a decision as to which reference table is to be populated first (e.g., where mutually-referencing parent and child entities can cause a relationship having a loop).

In one embodiment, a user might use dashboard 134 to launch processing to identify circular relationships. Strictly as an example, the following steps can be followed:

Step1: Generate a "Multilevel Entity Dependency Matrix (MEDM)" for the entire schema.

Step 2: For each root child entity, search the root child to determine if the root child is identified as an "Immediate parent" at any level other than depth 1 (return Boolean TRUE) or not (return Boolean FALSE).

Step3: If the search in Step 2 returns any Boolean TRUE value, then the root child has at least one circular reference. Note the example given in the multilevel schema data structure $110_2$, showing the entire the example branches of relationships.

TABLE 5

Example

| Root_Child_Table | Child_Table | Immediate_Parent | Depth | Optionality |
|---|---|---|---|---|
| HDM_ENC | HDM_ENC | HDM_PT | 1 | N |
| HDM_ENC | HDM_ENC | HDM_PT_ACCT | 1 | Y |
| HDM_ENC | HDM_PT | HDM_IND_PRTY | 2 | N |
| HDM_ENC | HDM_PT_ACCT | HDM_PT | 2 | N |
| HDM_ENC | HDM_IND_PRTY | HDM_ENC | 3 | N |

The above example has a circular relationship as shown below:

Encounter (0)>Individual Party (1)>Patient (2)>Encounter (3)

Pseudo Code—Identification if CRI:

```
SELECT ROOT_CHILD_TBL, CHILD_TBL, IMMIDIATE_PARENT,
DEPTH FROM (SELECT ROOT_CHILD_TBL, DEPTH FROM
TABLE2 WHERE IMMIDIATE_PARENT = ROOT_CHILD_TBL)
T, TABLE1 DEP
WHERE DEP.ROOT_CHILD_TBL = T.ROOT_CHILD_TBL AND
DEP.DEPTH<= T.DEPTH
```

That is, in one case, the root child is HDM_ENC and the same table is getting repeated as Immediate Parent to other tables. So it is thus calculated that there is a loop.

In most situations, circular references are anomalies that need to be corrected, and in some such cases a remover engine 426 can be used to recommend (and/or effect) possible corrections to the user.

Redundant Referential Integrity (RRI)

A redundant relationship is a relationship pattern where a given child table is connected with a parent table with more than one relationship branch. A redundant relationship does not necessarily mean there is an illegal database schema anomaly. There are scenarios where a same parent can be connected with a child as a different role. This may be a valid relationship since roles are different. Nevertheless, the redundant referential integrity analyzer 404 serves to identify redundant relationships for further analysis (or removal).

Pseudo Code—Identification of RRI:

```
SELECT DISTINCT ROOT_CHILD_TBL, IMMIDIATE_PARENT,
DEPTH FROM (SELECT ROOT_CHILD_TBL,
IMMIDIATE_PARENT, DEPTH, COUNT (CHILD_TBL) OVER
(PARTITION BY ROOT_CHILD_TBL, IMMIDIATE_PARENT
ORDER BY DEPTH) CNT FROM TABLE2) T WHERE T.CNT>1;
```

Figure 5:
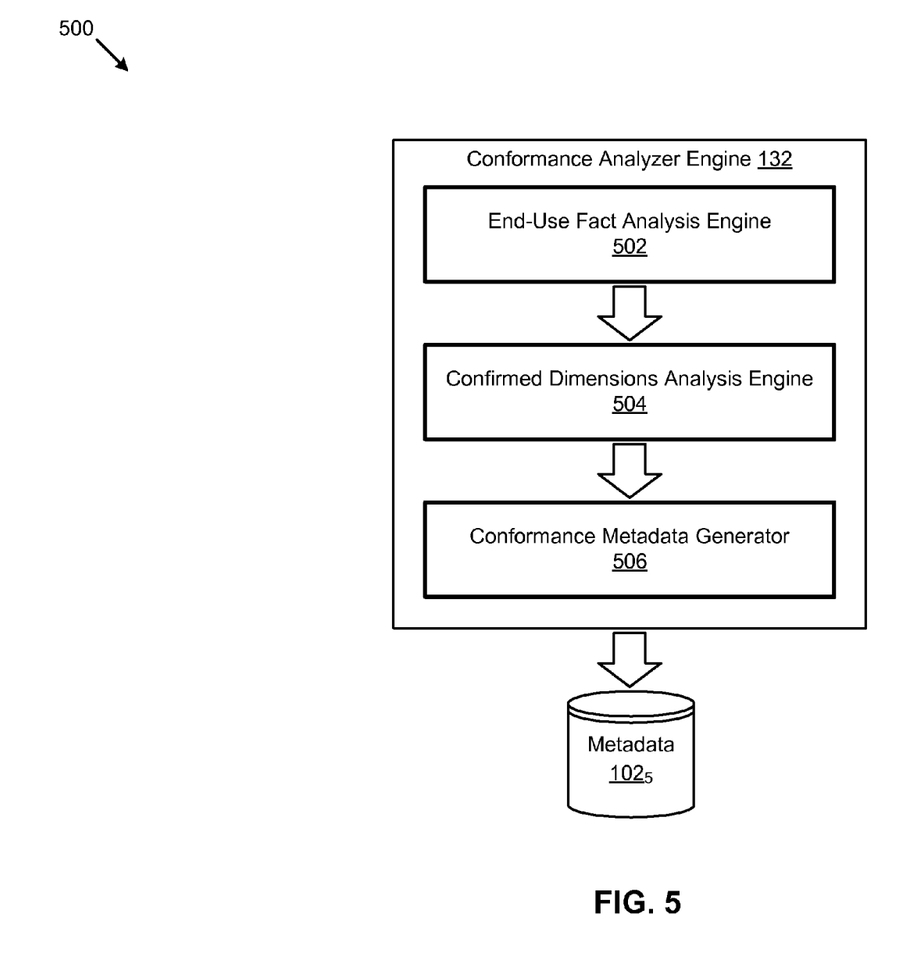
FIG. 5 depicts a conformance analyzer subsystem used in a system for data model optimization using multilevel entity dependency analytics, according to some embodiments.

FIG. 5 depicts a conformance analyzer subsystem 500 used in a system for data model optimization using multilevel entity dependency analytics. As an option, the present conformance analyzer subsystem 500 may be implemented in the context of the architecture and functionality of the embodiments described herein. Also, the conformance analyzer subsystem 500 or any aspect therein may be implemented in any desired environment.

As shown, the conformance analyzer engine 132 (introduced in FIG. 1) includes an end-use fact analysis engine 502, a confirmed dimensions analysis engine 504, and a conformance metadata generator 506. The conformance analyzer subsystem 500 includes outputs in the form of metadata $102_5$. Multilevel Entity Dependency is queried to identify entities that have the potential to be a conformed dimension (e.g., in an "enterprise data warehousing" environment). Entity conformance is determined using a number of subject areas that are dependent on that entity. Entities with very high conformity can act as a "bridge" and can be categorized as master entities. A subject area can be defined as a business process for which data is stored in various entities. Normally within a subject area there are transactional tables with higher loading sequence order that are dependent on multiple master tables. An entity is considered to be highly conformed if it has a low loading sequence number and its number of occurrences in a parental path having a root child as a transactional entity includes an immediate_parent at a higher depth.

ADDITIONAL EMBODIMENTS OF THE DISCLOSURE

Figure 6:
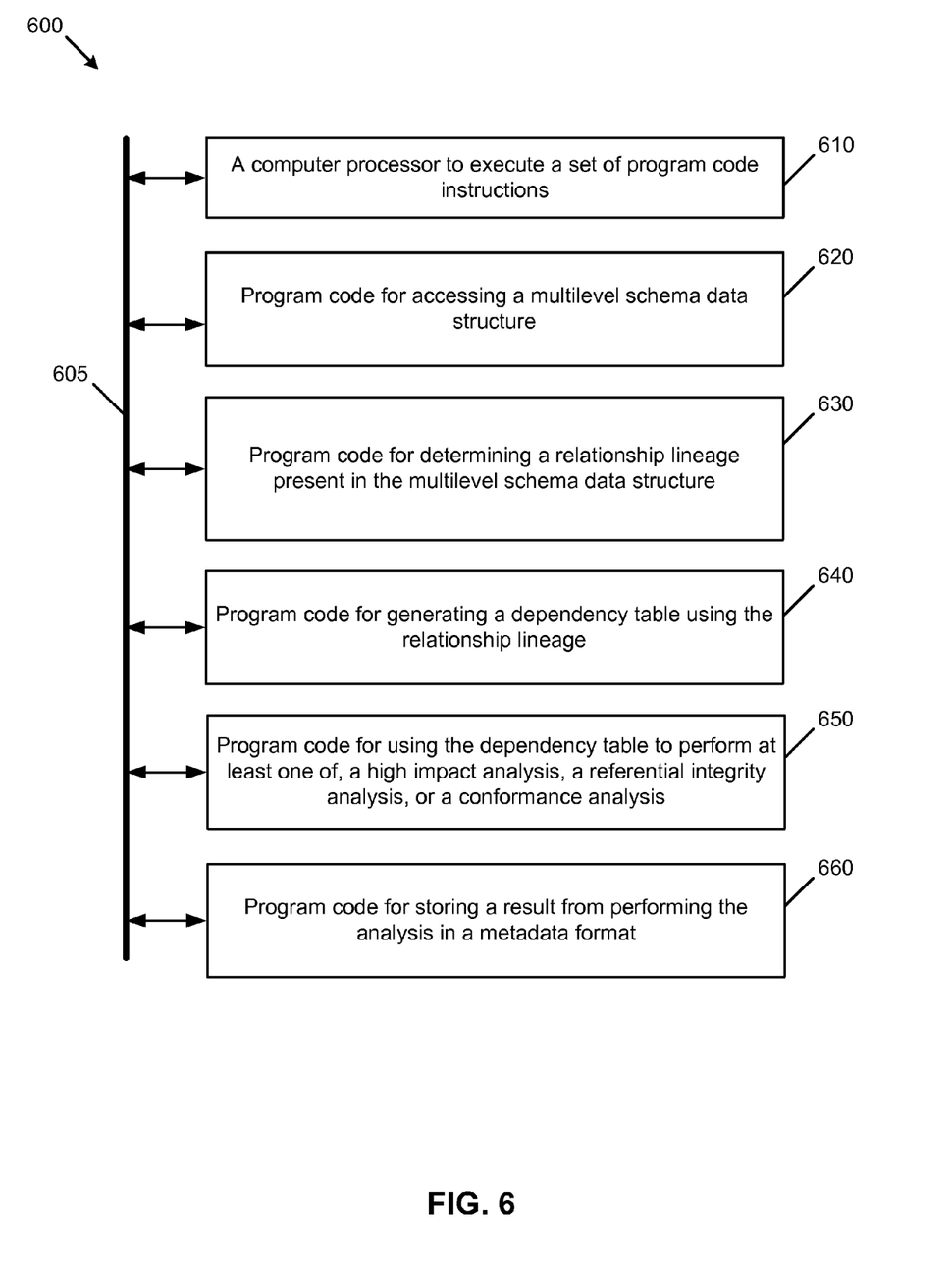
FIG. 6 depicts a block diagram of a system to perform certain functions of a computer system.

FIG. 6 depicts a block diagram of a system to perform certain functions of a computer system. As an option, the present system 600 may be implemented in the context of the architecture and functionality of the embodiments described herein. Of course, however, the system 600 or any operation therein may be carried out in any desired environment. As shown, system 600 comprises at least one processor and at least one memory, the memory serving to store program instructions corresponding to the operations of the system. As shown, an operation can be implemented in whole or in part using program instructions accessible by a module. The modules are connected to a communication path 605, and any operation can communicate with other operations over communication path 605. The modules of the system can, individually or in combination, perform method operations within system 600. Any operations performed within system 600 may be performed in any order unless as may be specified in the claims. The embodiment of FIG. 6 implements a portion of a computer system, shown as system 600, comprising a computer processor to execute a set of program code instructions (see module 610) and modules for accessing memory to hold program code instructions to perform: accessing a multilevel schema data structure (see module 620); determining a relationship lineage present in the multilevel schema data structure (see module 630); generating a dependency table using the relationship lineage (see module 640); using the dependency table to perform at least one of, a high impact analysis, a referential integrity analysis, or a conformance analysis (see module 650); and storing a result from the performing at least one of, a high impact analysis, a referential integrity analysis, or a conformance analysis in a metadata format (see module 660).

System Architecture Overview

Figure 7:
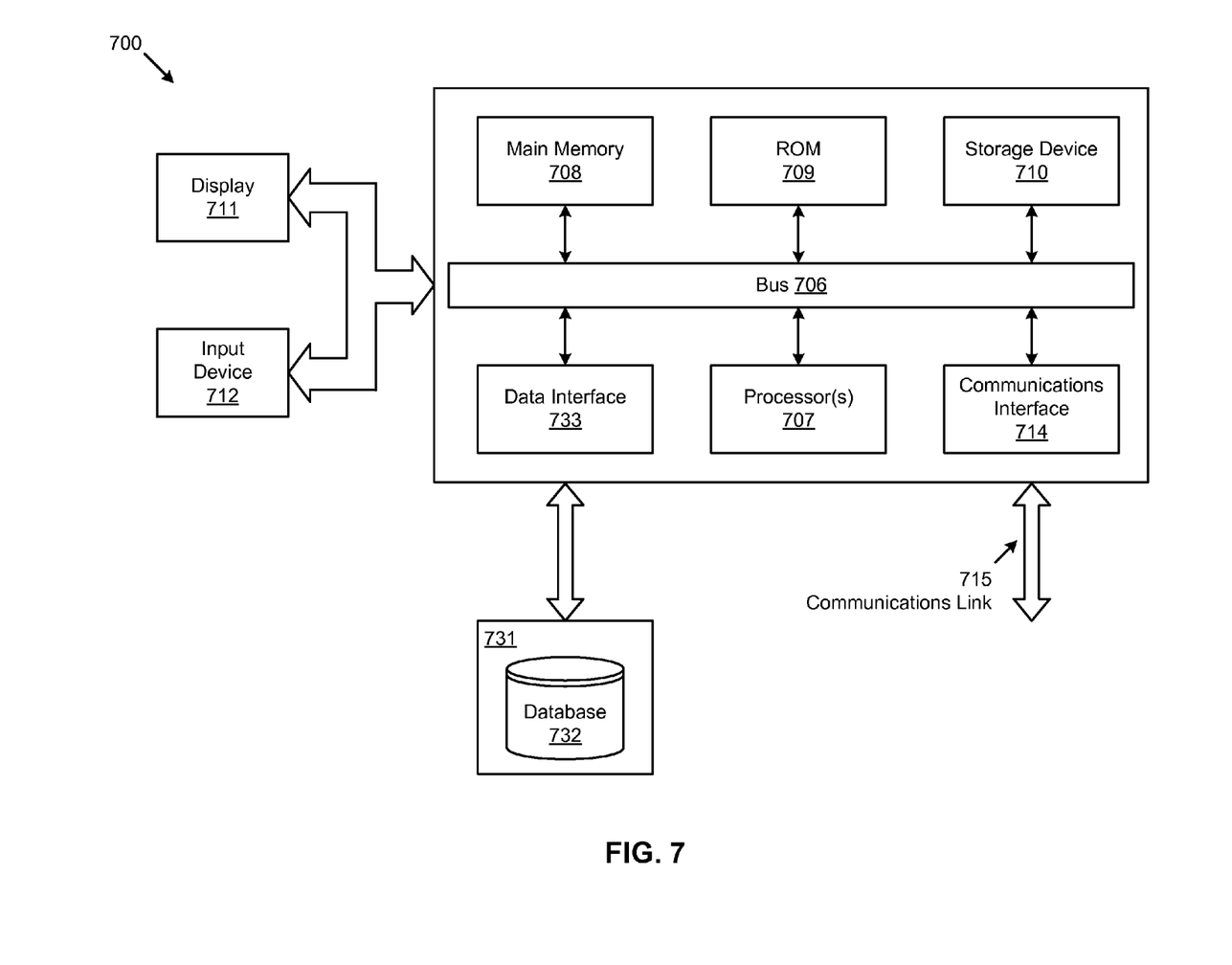
FIG. 7 depicts a block diagram of an instance of a computer system suitable for implementing an embodiment of the present disclosure.

FIG. 7 depicts a block diagram of an instance of a computer system 700 suitable for implementing an embodiment of the present disclosure. Computer system 700 includes a bus 706 or other communication mechanism for communicating information, which interconnects subsystems and devices, such as a processor 707, a system memory 708 (e.g., RAM), a static storage device (e.g., ROM 709), a disk drive 710 (e.g., magnetic or optical), a data interface 733, a communication interface 714 (e.g., modem or Ethernet card), a display 711 (e.g., CRT or LCD), input devices 712 (e.g., keyboard, cursor control), and an external data repository 731.

According to one embodiment of the disclosure, computer system 700 performs specific operations by processor 707 executing one or more sequences of one or more instructions contained in system memory 708. Such instructions may be read into system memory 708 from another computer readable/usable medium, such as a static storage device or a disk drive 710. In alternative embodiments, hard-wired circuitry may be used in place of or in combination with software instructions to implement the disclosure. Thus, embodiments of the disclosure are not limited to any specific combination of hardware circuitry and/or software. In one embodiment, the term "logic" shall mean any combination of software or hardware that is used to implement all or part of the disclosure.

The term "computer readable medium" or "computer usable medium" as used herein refers to any medium that participates in providing instructions to processor 707 for execution. Such a medium may take many forms, including but not limited to, non-volatile media and volatile media. Non-volatile media includes, for example, optical or magnetic disks, such as disk drive 710. Volatile media includes dynamic memory, such as system memory 708.

Common forms of computer readable media includes, for example, floppy disk, flexible disk, hard disk, magnetic tape, or any other magnetic medium; CD-ROM or any other optical medium; punch cards, paper tape, or any other physical medium with patterns of holes; RAM, PROM, EPROM, FLASH-EPROM, or any other memory chip or cartridge, or any other non-transitory medium from which a computer can read data.

In an embodiment of the disclosure, execution of the sequences of instructions to practice the disclosure is performed by a single instance of the computer system 700. According to certain embodiments of the disclosure, two or more computer systems 700 coupled by a communications link 715 (e.g., LAN, PTSN, or wireless network) may perform the sequence of instructions required to practice the disclosure in coordination with one another.

Computer system 700 may transmit and receive messages, data, and instructions, including programs (e.g., application code), through communications link 715 and communication interface 714. Received program code may be executed by processor 707 as it is received, and/or stored in disk drive 710 or other non-volatile storage for later execution. Computer system 700 may communicate through a data interface 733 to a database 732 on an external data repository 731. A module as used herein can be implemented using any mix of any portions of the system memory 708, and any extent of hard-wired circuitry including hard-wired circuitry embodied as a processor 707.

In the foregoing specification, the disclosure has been described with reference to specific embodiments thereof. It will, however, be evident that various modifications and changes may be made thereto without departing from the broader spirit and scope of the disclosure. For example, the above-described process flows are described with reference to a particular ordering of process actions. However, the ordering of many of the described process actions may be changed without affecting the scope or operation of the disclosure. The specification and drawings are, accordingly, to be regarded in an illustrative sense rather than restrictive sense.

What is claimed is:

1. A computer implemented method for data model optimization using multilevel entity dependency analytics, the method comprising:
   accessing a multilevel schema data structure;
   determining, using a computer, a dependency relationship lineage between schema entities present in the multilevel schema data structure;
   generating a dependency table using the dependency relationship lineage, the dependency table comprising at least one multilevel dependency relationship between schema entities having a depth of two or more;

using the dependency table to perform at least one analysis comprising at least one of, a high impact analysis, a referential integrity analysis, or a conformance analysis; and storing a result from the analysis in a stored metadata format.

2. The method of claim 1, further comprising using the dependency table to perform analyses comprising an entity loading sequence analysis.

3. The method of claim 1, wherein the stored metadata format is at least one of, an XML format, a binary format, a message format, or a relational database table.

4. The method of claim 1, wherein performing the high impact analysis comprises a change request for the multilevel schema data structure.

5. The method of claim 1, further comprising reading a script to automate regression testing.

6. The method of claim 1, further comprising receiving the stored metadata format into a data model change engine.

7. The method of claim 1, further comprising recommending corrections.

8. A computer system for data model optimization using multilevel entity dependency analytics, comprising:
a computer processor to execute a set of program code instructions; and
a memory to hold the program code instructions, in which the program code instructions comprises program code to perform,
accessing a multilevel schema data structure;
determining a dependency relationship lineage between schema entities present in the multilevel schema data structure;
generating a dependency table using the dependency relationship lineage, the dependency table comprising at least one multilevel dependency relationship between schema entities having a depth of two or more;
using the dependency table to perform at least one analysis comprising at least one of, a high impact analysis, a referential integrity analysis, or a conformance analysis; and
storing a result from the analysis in a stored metadata format.

9. The computer system of claim 8, further comprising using the dependency table to perform analyses comprising an entity loading sequence analysis.

10. The computer system of claim 8, wherein the stored metadata format is at least one of, an XML format, a binary format, a message format, or a relational database table.

11. The computer system of claim 8, wherein performing the high impact analysis comprises a change request for the multilevel schema data structure.

12. The computer system of claim 8, further comprising reading a script to automate regression testing.

13. The computer system of claim 8, further comprising receiving the stored metadata format into a data model change engine.

14. The computer system of claim 8, further comprising recommending corrections.

15. A computer program product embodied in a non-transitory computer readable medium, the computer readable medium having stored thereon a sequence of instructions which, when executed by a processor causes the processor to execute a process to implement data model optimization using multilevel entity dependency analytics, the process comprising:
accessing a multilevel schema data structure;
determining a dependency relationship lineage between schema entities present in the multilevel schema data structure;
generating a dependency table using the dependency relationship lineage, the dependency table comprising at least one multilevel dependency relationship between schema entities having a depth of two or more;
using the dependency table to perform at least one analysis comprising at least one of, a high impact analysis, a referential integrity analysis, or a conformance analysis; and
storing a result from the analysis in a stored metadata format.

16. The computer program product of claim 15, further comprising using the dependency table to perform analyses comprising an entity loading sequence analysis.

17. The computer program product of claim 15, wherein the stored metadata format is at least one of, an XML format, a binary format, a message format, or a relational database table.

18. The computer program product of claim 15, wherein performing the high impact analysis comprises a change request for the multilevel schema data structure.

19. The computer program product of claim 15, further comprising reading a script to automate regression testing.

20. The computer program product of claim 15, further comprising receiving the stored metadata format into a data model change engine.

* * * * *

UNITED STATES PATENT AND TRADEMARK OFFICE
CERTIFICATE OF CORRECTION

Page 1 of 2

PATENT NO. : 8,972,460 B2
APPLICATION NO. : 13/658651
DATED : March 3, 2015
INVENTOR(S) : Das It is certified that error appears in the above-identified patent and that said Letters Patent is hereby corrected as shown below:

ON THE TITLE PAGE

Column 2, under Abstract, line 1, after "for" delete "of".

In the illustrative figure, below Depth 3, line 1, delete "Invididual" and insert -- Individual --, therefor.

In the illustrative figure, under Reference Numeral 124, line 3, delete "Gererator" and insert -- Generator --, therefor.

IN THE DRAWINGS

On sheet 1 of 7, in drawings, in figure 1, Below Depth 3, line 1, delete "Invididual" and insert -- Individual --, therefor.

On sheet 1 of 7, in drawings, in figure 1, under Reference Numeral 124, line 3, delete "Gererator" and insert -- Generator --, therefor.

On sheet 2 of 7, in drawings, in figure 2, under Max Depth1, line 1, delete "Invididual" and insert -- Individual --, therefor.

On sheet 2 of 7, in drawings, in figure 2, under Reference Numeral 224, line 3, delete "Gererator" and insert -- Generator --, therefor.

IN THE SPECIFICATION

In column 6, line 26, delete "Step 2:" and insert -- Step2: --, therefor.

In column 6, line 46, delete "IMMIDIATE" and insert -- IMMEDIATE --, therefor.

Signed and Sealed this
Twentieth Day of October, 2015

Michelle K. Lee
*Director of the United States Patent and Trademark Office*

CERTIFICATE OF CORRECTION (continued)
U.S. Pat. No. 8,972,460 B2

IN THE SPECIFICATION

In column 10, line 56, delete "0" and insert -- O --, therefor.

In column 10, line 60, delete "0" and insert -- O --, therefor.

In column 11, line 45, delete "Step 2:" and insert -- Step2: --, therefor.

In column 12, line 6, delete "IMMIDIATE" and insert -- IMMEDIATE --, therefor.

In column 12, line 8, delete "IMMIDIATE" and insert -- IMMEDIATE --, therefor.

In column 12, line 32, delete "IMMIDIATE" and insert -- IMMEDIATE --, therefor.

In column 12, line 34, delete "IMMIDIATE" and insert -- IMMEDIATE --, therefor.

In column 12, line 35, delete "IMMIDIATE" and insert -- IMMEDIATE --, therefor.